(12) United States Patent
Wago et al.

(10) Patent No.: US 10,655,164 B2
(45) Date of Patent: *May 19, 2020

(54) SINGLE MOLECULE DNA SEQUENCING METHOD USING CONFINED NANO-FLUIDIC CHANNEL AND SUB-NANOMETER ELECTRODE GAP

(71) Applicant: SEAGATE TECHNOLOGY LLC, Cupertino, CA (US)

(72) Inventors: Koichi Wago, Sunnyvale, CA (US); ShuaiGang Xiao, Fremont, CA (US); Xiaomin Yang, Livermore, CA (US); Kim Yang Lee, Fremont, CA (US); David S. Kuo, Palo Alto, CA (US); Thomas Young Chang, Menlo Park, CA (US)

(73) Assignee: SEAGATE TECHNOLOGY LLC, Fremont, CA (US)

(*) Notice: Subject to any disclaimer, the term of this patent is extended or adjusted under 35 U.S.C. 154(b) by 69 days.

This patent is subject to a terminal disclaimer.

(21) Appl. No.: 15/886,442

(22) Filed: Feb. 1, 2018

(65) Prior Publication Data

US 2018/0216169 A1 Aug. 2, 2018

Related U.S. Application Data

(60) Provisional application No. 62/453,270, filed on Feb. 1, 2017.

(51) Int. Cl.
*G01N 27/327* (2006.01)
*C12Q 1/6825* (2018.01)
(Continued)

(52) U.S. Cl.
CPC ...... *C12Q 1/6825* (2013.01); *B01L 3/502761* (2013.01); *C12Q 1/6806* (2013.01);
(Continued)

(58) Field of Classification Search
CPC .................................. G01N 33/48721
See application file for complete search history.

(56) References Cited

U.S. PATENT DOCUMENTS 6,627,067 B1 * 9/2003 Branton ............... B24B 37/013
204/403.06
8,105,471 B1 * 1/2012 Han .................. G01N 27/44752
204/451

(Continued)

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.

(Continued)

*Primary Examiner* — Alexander S Noguerola
(74) *Attorney, Agent, or Firm* — Holzer Patel Drennan

(57) ABSTRACT

Apparatus and methods to sequence DNA. A DNA sequencing device includes a passage, a first electrode, and a second electrode. The passage has a width and a length. The first and second electrodes are exposed within the passage and spaced apart from each other to form an electrode gap. The electrode gap is no greater than about 2 nm. The DNA sequencing device is operable to measure with the first and second electrodes a change in electronic signal in response to nucleotides of a DNA strand passing through the electrode gap.

17 Claims, 4 Drawing Sheets

(51) Int. Cl.
| | |
|---|---|
| C12Q 1/6874 | (2018.01) |
| G01N 27/447 | (2006.01) |
| B01L 3/00 | (2006.01) |
| C12Q 1/6837 | (2018.01) |
| G01N 27/414 | (2006.01) |
| C12Q 1/6806 | (2018.01) |
| G01N 33/487 | (2006.01) |
| C12Q 1/6869 | (2018.01) |

(52) U.S. Cl.
CPC ......... *C12Q 1/6837* (2013.01); *C12Q 1/6869* (2013.01); *C12Q 1/6874* (2013.01); *G01N 27/4145* (2013.01); *G01N 27/44791* (2013.01); *G01N 33/48721* (2013.01)

(56) References Cited

U.S. PATENT DOCUMENTS

| | | |
|---|---|---|
| 9,410,923 B2 | 8/2016 | Sauer et al. |
| 2002/0039737 A1* | 4/2002 | Chan ................ B01L 3/502761 435/6.18 |
| 2010/0267158 A1* | 10/2010 | Chou ................ B01L 3/502761 436/94 |
| 2013/0334047 A1* | 12/2013 | Jeong .................... G01N 27/00 204/452 |
| 2017/0146510 A1* | 5/2017 | Ikeda ............... G01N 33/48721 |

OTHER PUBLICATIONS

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

KE, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 59 pages.

* cited by examiner

SINGLE MOLECULE DNA SEQUENCING METHOD USING CONFINED NANO-FLUIDIC CHANNEL AND SUB-NANOMETER ELECTRODE GAP

RELATED APPLICATIONS

This application claims the benefit of the filing date of U.S. Provisional Application No. 62/453,270, filed on 1 Feb. 2017, and entitled SINGLE-MOLECULE DNA SEQUENCING METHOD USING CONFINED NANO-FLUIDIC CHANNEL AND SUB-NANOMETER ELECTRODE GAP, the disclosure of which is incorporated in its entirety by this reference.

SUMMARY

One aspect of the present disclosure relates to a DNA sequencing device that includes a passage, a first electrode, and a second electrode. The passage has a width and a length. The first and second electrodes are exposed within the passage and spaced apart from each other to form an electrode gap. The electrode gap is no greater than about 2 nm. The DNA sequencing device is operable to measure with the first and second electrodes a change in electronic signal in response to nucleotides of a DNA strand passing through the electrode gap.

At least one of the first and second electrodes may be movable to adjust a size of the electrode gap. The first electrode may be arranged parallel with the length of the passage and the second electrode may be arranged perpendicular to the first electrode. The device may further include a substrate, and the passage may be formed in the substrate and at least the first electrode may be positioned in the substrate. The electrode gap may be in the range of about 0.3 nm to about 1 nm. The electrodes may be positioned vertically relative to each other at locations above and below the passage. The electrodes may be positioned laterally relative to each other at locations on opposing sides of the passage. At least one of the first and second electrodes may be embedded in a structure in which the passage is formed. At least one of the first and second electrodes may be arranged perpendicular to the passage. The passage may be formed as a nanochannel, and the nanochannel may have a width in the range of about 5 nm to about 50 nm.

Another aspect of the present disclosure relates to a method of forming a device to sequence DNA. The method includes forming a passage in a substrate, and forming first and second electrodes that are exposed within the passage and spaced apart from each other to form an electrode gap. The electrode gap is no greater than about 2 nm. The electrodes are operable to measure a change in electronic signal as a DNA strand passes through the electrode gap.

The method may include embedding at least one of the first and second electrodes in the substrate. The method may include orienting the first and second electrodes perpendicular to each other. The passage may be configured as a nanochannel, and the method further includes orienting the first and second electrodes parallel to each other and perpendicular to the nanochannel. The passage may be configured as a nanochannel, and the method may further include orienting the first and second electrodes laterally relative to each other and perpendicular to the nanochannel. The method may include orienting the first and second electrodes vertically relative to each other. Forming the passage may include using at least one of electron-beam lithography (EBL), reactive-ion etching (RIE), and spin-on-glass (SOG). The passage may be configured as a nanochannel, and the method may include forming the nanochannel with a width in the range of about 5 nm to about 50 nm. The passage may be formed as a nanopore.

Another aspect of the present disclosure relates to a method of sequencing DNA. The method includes providing a DNA sequencing device having a passage formed in a substrate, and first and second electrodes, the first and second electrodes being exposed within the passage and spaced apart from each other to form an electrode gap, the electrode gap being no greater than about 2 nm. The method also includes passing a DNA strand through the electrode gap, and measuring an electronic signal using the first and second electrodes as the DNA strand passes through the electrode gap, the electronic signal corresponding to at least one nucleotide of the DNA strand.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Despite considerable efforts, DNA sequencing today still suffers from high costs and low speeds. To address these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

One prior approach includes a nanopore with a gap electrode. However, the nanopore has a diameter greater than 10 nm, and a related electrode gap of greater than 10 nm, which creates problems for accurately reading individual nucleotides of a DNA strand, and difficulties in directing the DNA strands into the nanopore.

The present disclosure generally relates to DNA sequencing, and more particularly relates to DNA sequencing devices having nanopores or nanochannels. The DNA sequencing devices also include nanoelectrodes. The present disclosure also relates to methods of fabricating DNA sequencing devices having an electrode gap that is less than 10 nm. The present disclosure also relates to DNA sequencing methods using such methods and devices.

The DNA sequencing devices of the present disclosure may use a confined nanopore or nanochannel, and embedded electrodes. The fabrication of the nanopore or nanochannel, and related electrodes may be precisely controlled in sub-nanometer level. The present disclosure also provides for single molecule DNA sequencing methods utilizing sub-nanometer fabrication that provides advances in the next generation sequencing (NGS) field.

Figure 1:
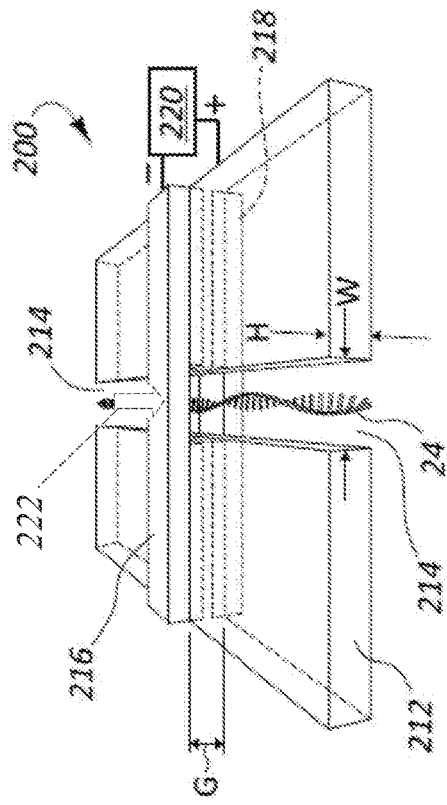
FIG. 1 shows a nanopore DNA sequencing device in accordance with the present disclosure.
Figure 2:
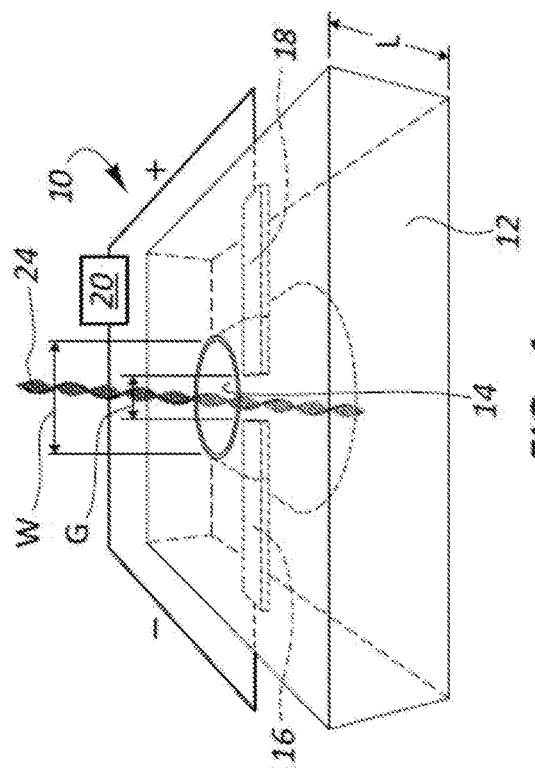
FIG. 2 shows a nanochannel DNA sequencing device in accordance with the present disclosure.
Figure 3:
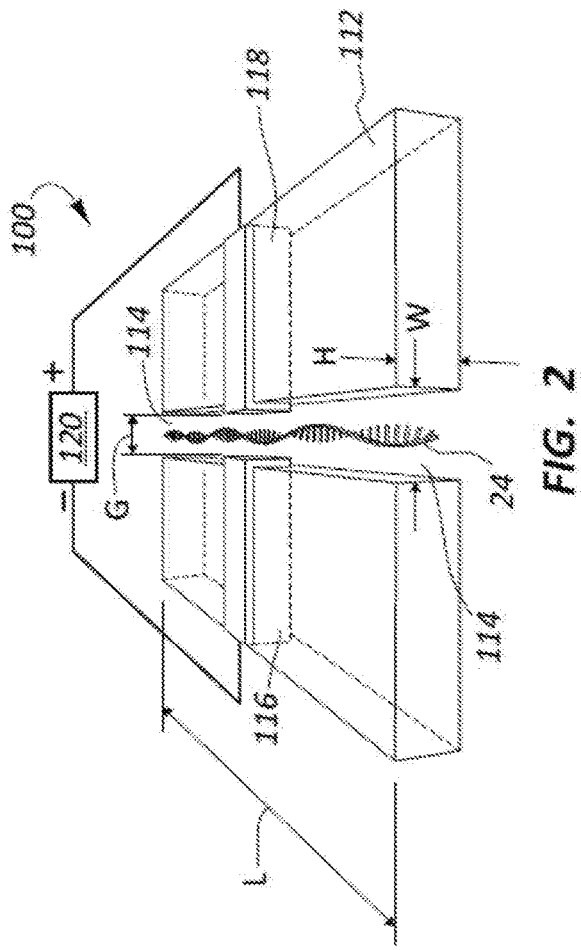
FIG. 3 shows another nanochannel DNA sequencing device in accordance with the present disclosure.

FIGS. 1-3 illustrate several DNA sequencing device embodiments that provide, for example, general concepts related to sequencing with quantum tunneling. The devices of FIGS. 1-3, and related methods of making and using the same, are exemplary only and have the potential to provide DNA sequencing at rates that are potentially orders of magnitude faster than current methods.

The devices of FIGS. 1-3 may provide direct measure of individual nucleotides of DNA strands rapidly and with relatively low cost. Among the various technologies being developed in this space, the nanopore- and nanochannel-based approaches shown in FIGS. 1-3, which measure a transverse signal across individual nucleotides of a DNA strand, have emerged as the most promising approaches. The general approach of the embodiments of FIGS. 1-3 involves electrically driving DNA and/or RNA strands through a nanochannel via ionic flow or a pressure gradient. As the strand pass a high resolution sensor embedded inside the channel (e.g., a nanoelectrode or electrode pair), the high spatial resolution sensor measures the unique properties of the individual nucleotides (A,T,C,G) of the DNA strand. One type of sensor would consist of a conductive electrode that measures the nucleotide's unique tunneling currents (e.g., electronic signals) thereby identifying and resolving the four unique nucleotide types.

There are several significant challenges associated with the prior approaches to direct measure DNA sequencing. One challenge relates to fabricating a sub-nanometer gap of the sensor electrode in a way that is controllable and repeatable with a high level of accuracy. The signal tunneling current depends exponentially to the gap distance. For example, the signal tunneling current may reduce by a factor of 1000× if spacing is increased between the electrode and the DNA nucleotide by only 0.5 nm. Another challenge relates to aligning the electrode gap within the nanopore or nanochannel. The electrode gap must be sized and positioned to ensure that DNA strands go through the electrode gap instead of bypassing the gap.

FIG. 1 illustrates schematically a DNA sequencing device 10 that may referred to as a nanopore device or nanopore DNA sequencing device. The device 10 includes a substrate 12, a passage 14 formed in the substrate 12, and first and second electrodes 16, 18. The device 10 may also include a controller 20 electrically coupled to the electrodes 16, 18 and operable to determine changes in electronic signals collected by the electrodes 16, 18. The controller 20 may be coupled to a computing system that includes, for example, a processor, memory, a user interface, an I/O controller, and the like.

The electrodes 16, 18 may together be referred to as a sensor, a sensing electrode, a nanoelectrode, an electrode probe, or the like. The electrodes 16, 18 may be at least partially embedded in the substrate 12. In some embodiments, one or both of the electrodes 16, 18 may be mounted to the substrate 12 either permanently or temporarily. In one embodiment, one of the electrodes 16, 18 is exposed in the passage 14 only at the time of making a measurement of a DNA strand 24 passing through the passage 14.

One or both of the electrodes 16, 18 may have a plate-like shape with a greater width and length than a thickness. In other embodiments, at least one of the electrodes 16, 18 may have an elongate (e.g., long and narrow) shape. At least one of the electrodes 16, 18 may have a cross-sectional shape that is pointed or tapered. Providing at least one of the electrodes 16, 18 with a pointed tip may provide an improved signal-to-noise ratio for the electronic signal measured between the electrodes 16, 18. In one example, the pointed tip is formed by a single atom or molecule, and may have a width that is equal to the width of the single atom or molecule. The pointed shape may be created using an additive process to building up the structure of the electrode, or a subtractive process to remove portions of the electrode to form the pointed structure.

The electrodes 16, 18 may be integrally formed with one or more substrates 12 as part of a method and/or process of forming the device 10. The electrodes 16, 18 may be formed using at least one of electron-beam lithography (EBL), reactive-ion etching (RIE), liftoff, sputter deposition, evaporation, atomic layer deposition (ALD), and spin-on-glass (SOG) process steps. The electrodes 16, 18 may comprise a conductive material such as, for example, a ferrous material. Some example ferrous materials include elements: Au, Pt and Ru.

The device 10 may include more than one pair of electrodes 16, 18 at spaced apart locations along a length L of the passage 14. Using more than one pair of electrodes 16, 18 may improve the accuracy of determining a DNA sequence for a given DNA strand 24 that passes through the passage 14.

The portions of electrodes 16, 18 that are exposed within the passage 14 are spaced apart a distance G, also referred to as an electrode gap G or a nanogap G. A DNA strand 24 may pass through the gap G as part of detecting individual nucleotides of the DNA strand 24.

The substrate 12 may comprise an insulating material such as, for example, C, $SiO_2$ or SiN. In one example, the substrate 12 has a thickness in the range of about 5 nm to about 20 nm, but may have a thickness up to at least 100 nm in some embodiments.

The passage 14 may be arranged vertically as shown in FIG. 1. In other examples, the passage 14 may be arranged at different orientations, such as horizontally. The passage 14 may be formed in the shape of a nanopore. The nanopore may have an inlet opening having a width W that leads to the passage 14. The inlet opening may have a circular shape. The width W may be in the range of, for example, about 5 nm to about 20 nm. The passage 14 may have a tapered shape that increases in width from the inlet to an outlet of the passage 14. In one example, the outlet has a width that is at least 2 times greater than the width W of the inlet.

A DNA strand 24 may be drawn into the passage 14 using, for example, electrophoresis to attract the DNA towards the passage 14. The small scale of the passage 14 means that the DNA strand 24 may be drawn through the hole as a long string, one nucleotide at a time. As it does so, each nucleotide on the DNA molecule may obstruct the electrode gap G between the electrodes 16, 18 to a different, characteristic degree. The amount of current which can pass between the electrodes 16, 18 at any given moment therefore varies depending on whether the nanopore is blocked by an A, C, G or T nucleotide, or a section of DNA that includes more than one of these nucleotides (kmer). The change in the amount of current measured by the electrodes (e.g., a change in electronic signal) as the DNA molecule passes through the passage 14 represents a direct reading of the DNA sequence. Other types of electronic signals (e.g., voltage, impedance, etc.) may be measured and/or detected in place of a current measurement as part of detecting particular nucleotides of the DNA strand.

Using the nanopore structure of device 10, a single molecule of DNA can be sequenced directly without the need for an intervening PCR amplification step or a chemical labelling step or the need for optical instrumentation to identify the chemical label. The versatility of the device 10 is underlined by the fact that it general can be applied to sequence chain-like genetic information carriers without knowing the exact structure of their building blocks.

FIG. 2 illustrates schematically an example DNA sequencing device 100 having a passage 114 and electrodes 116, 118 provided in a substrate 112. The passage 114 may be configured as a confined nanochannel (also referred to as a nanofluidics channel). The electrodes 116, 118 may be embedded in the substrate 112. The passage 114 and electrodes 116, 118 may be oriented in a common plane that is referred to as an in-plane orientation. The electrodes 116, 118 may generally be referred to, for example, as a nanoelectrode, an electrode probe(s), a sensor, a sensing electrode, or the like. The electrode members shown in FIG. 2 are arranged end-to-end, and may generally be described as having a side-by-side or lateral arrangement.

Ends of the electrodes 116, 118 may be exposed within the passage 114. A spacing or gap G between the ends of the electrodes 116, 118 may be positioned and/or exposed within the passage 114. The gap G may be precisely controlled within a predetermined range, such as no greater than 2 nm, a range of about 0.3 nm to about 2 nm, a range of about 0.3 nm to about 1 nm, or about 1 nm.

The passage 114 may have a width dimension that is equal to or less than the gap G dimension. Typically, the passage 114 has a width W in the range of about 5 nm to about 50 nm, and more particularly in the range of about 10 nm to about 20 nm. Walls of the passage 114 may be relatively planar and be arranged parallel to each other. Typically, the passage 114 may have a greater height H than width W dimension. The passage 114 may also have a length L. Typically, the length L is greater than a length of a single DNA strand. The electrodes 116, 118 may have a similar height to the height of the passage 114.

The substrate 110 may comprise an insulating material such as, for example, C, $SiO_2$ or SiN. In one example, the substrate 110 has a thickness in the range of about 5 nm to about 20 nm, but may have a thickness up to at least 100 nm in some embodiments.

The passage 114 may be arranged horizontally, as shown in FIG. 2. In other examples, the passage 114 may be arranged at different orientations, such as at an angle relative to a horizontal plane. The passage 114 may be formed in the shape of a channel. The channel may have a width W that leads to the electrode gap G. The passage 114 may have a rectangular cross-sectional shape. The gap G may have a different cross-sectional shape and/or size as compared to that of the passage 114. The width W may be in the range of, for example, about 5 nm to about 20 nm A DNA strand 24 may be drawn into the passage 114 using, for example, electrophoresis to attract the DNA towards the passage 114. The small scale of the passage 114 means that the DNA strand 24 may be drawn into an inlet end of the passage 114 as a long string, one nucleotide at a time. As the DNA strand 24 passes through the passage 114, each nucleotide on the DNA strand 24 may obstruct the electrode gap G between the electrodes 116, 118 to a different, characteristic degree. The amount of current which can pass between the electrodes 116, 118 at any given moment therefore varies depending on whether the nanopore is blocked by an A, C, G or T nucleotide, or a section of DNA that includes more than one of these nucleotides (kmer). The change in the current measured by the electrodes as the DNA molecule passes through the passage 114 represents a direct reading of the DNA sequence.

Using the channel structure of device 100, a single molecule of DNA can be sequenced directly without the need for an intervening PCR amplification step or a chemical labelling step or the need for optical instrumentation to identify the chemical label. The versatility of the device 110 is underlined by the fact that it general can be applied to sequence chain-like genetic information carriers without knowing the exact structure of their building blocks.

FIG. 3 illustrates schematically an example DNA sequencing device 200 having a passage 214 and electrodes 216, 218 provided in a substrate 212. The passage 214 may be configured as a confined nanochannel (also referred to as a nanofluidics channel). The electrodes 216, 218 may be embedded in the substrate 212. The passage 214 and electrodes 216, 218 may be oriented in a common plane that is referred to as an in-plane orientation. The electrodes 216, 218 may generally be referred to, for example, as a nanoelectrode, an electrode probe(s), a sensor, a sensing electrode, or the like. The electrode members shown in FIG. 2 are arranged vertically relative to each other, and may generally be described as having a up/down, over/under, or vertical arrangement.

Ends of the electrodes 216, 218 may be exposed within the passage 214. A spacing or gap G between the ends of the electrodes 216, 218 may be positioned and/or exposed within the passage 214. The gap G may be precisely controlled within a predetermined range, such as no greater than 2 nm, a range of about 0.3 nm to about 2 nm, a range of about 0.3 nm to about 1 nm, or about 1 nm.

The passage 214 may have a width dimension that is equal to or less than the gap G dimension. Typically, the passage 214 has a width W in the range of about 5 nm to about 50 nm, and more particularly in the range of about 10 nm to about 20 nm. Walls of the passage 214 may be relatively planar and be arranged parallel to each other. Typically, the passage 214 may have a greater height H than width W dimension. The electrodes 216, 218 may have a similar height to the height of the passage 214.

The substrate 210 may comprise an insulating material such as, for example, C, $SiO_2$ or SiN. In one example, the substrate 210 has a thickness in the range of about 5 nm to about 20 nm, but may have a thickness up to at least 200 nm in some embodiments.

The passage 214 may be arranged horizontally, as shown in FIG. 2. In other examples, the passage 214 may be arranged at different orientations, such as at an angle relative to a horizontal plane. The passage 214 may be formed in the shape of a channel. The channel may have a width W that leads to the electrode gap G. The passage 214 may have a rectangular cross-sectional shape. The gap G may have a different cross-sectional shape and/or size as compared to that of the passage 214. The width W may be in the range of, for example, about 5 nm to about 20 nm A DNA strand 24 may be drawn into the passage 214 using, for example, electrophoresis to attract the DNA towards the passage 214. The small scale of the passage 214 means that the DNA strand 24 may be drawn into an inlet end of the passage 214 as a long string, one nucleotide at a time. As the DNA strand 24 passes through the passage 214, each nucleotide on the DNA strand 24 may obstruct the electrode gap G between the electrodes 216, 218 to a different, characteristic degree. The amount of current which can pass between the electrodes 216, 218 at any given moment therefore varies depending on whether the nanopore is blocked by an A, C, G or T nucleotide, or a section of DNA that includes more than one of these nucleotides (kmer). The change in the current measured by the electrodes as the DNA molecule passes through the passage 214 represents a direct reading of the DNA sequence.

Using the channel structure of device 200, a single molecule of DNA can be sequenced directly without the need for an intervening PCR amplification step or a chemical labelling step or the need for optical instrumentation to identify the chemical label. The versatility of the device 200 is underlined by the fact that it general can be applied to sequence chain-like genetic information carriers without knowing the exact structure of their building blocks.

The electrode gap G may be controlled to a specified size using an actuator 222. In one example, the actuator 222 is a heater that provides expansion of material (e.g., substrate 212) within which one or more electrode members 216, 218 is embedded, thus causing relative movement between the electrode members 216, 218 to alter the gap G size. In another example, the actuator 222 is a cooling member that provides contraction of material (e.g., substrate 212) within which one or more electrode members 216, 218 is embedded, thus causing relative movement between the electrode members 216, 218 to alter the gap G size. The actuator 222 may provide sub-nanometer control of the gap G. In another example, the actuator 222 applies a force to one or more of the electrodes 216, 218, or is inserted directly into the passage 214 and acts as one of the electrodes 216, 218, to alter a size of gap G.

Various fabrication methods, techniques, materials, and processes may be used to form the DNA sequencing devices disclosed herein. For example, sputter deposition, spin-on-glass (SOG), patterning using deep ultraviolet (DUV) lithography, 193 nm lithography, e-beam lithography, or nanoimprint lithography (NIL), reactive ion etching (RIE), and wet etching may be used to form various layers, structures and the like as part of a fabrication process.

Figure 4:
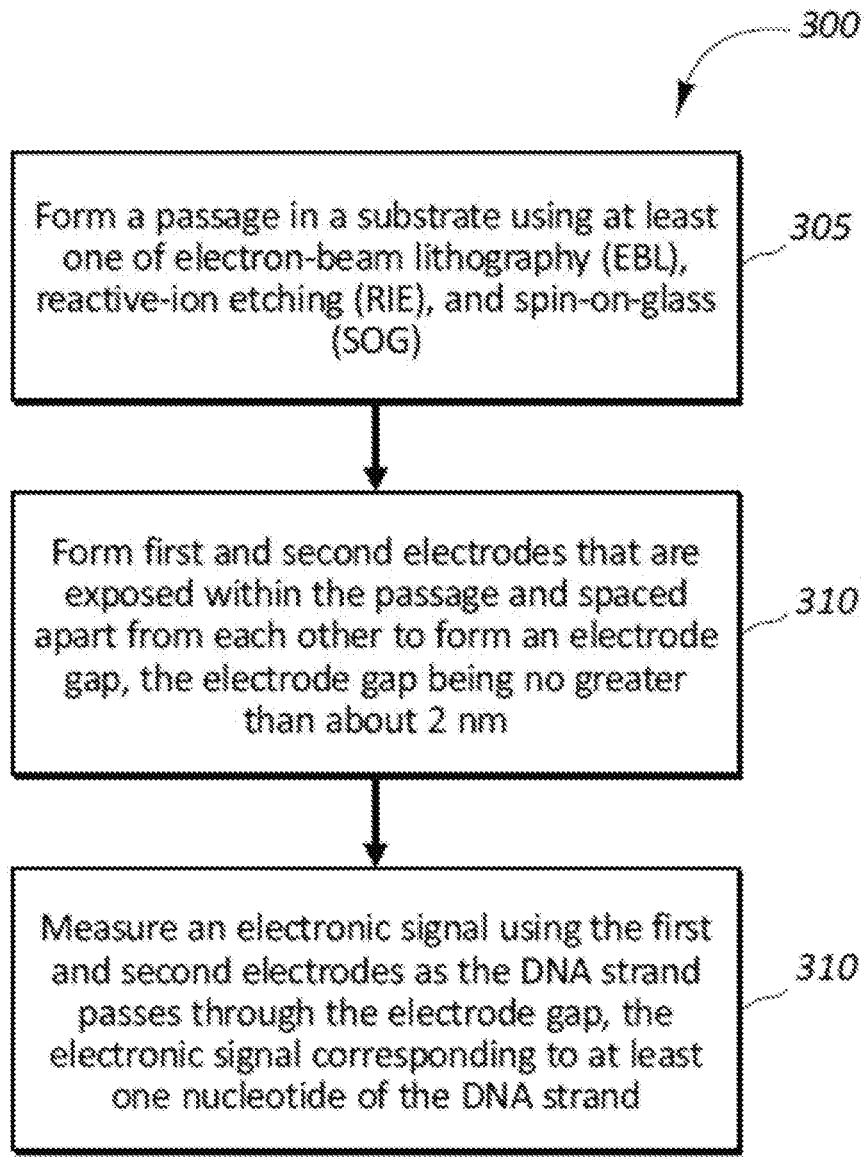
FIG. 4 is a flow diagram illustrating an example method in accordance with the present disclosure.

FIG. 4 illustrates an example method of manufacturing and/or fabricating a DNA sequencing device. At block 305, the method includes forming a passage in a substrate using at least one of electron-beam lithography (EBL), reactive-ion etching (RIE), and spin-on-glass (SOG). As noted above, other fabrication steps may be used to form the passage including, for example, sputter deposition, patterning using deep ultraviolet (DUV) lithography, 193 nm lithography, e-beam lithography, nanoimprint lithography (NIL), and wet etching. The passage may be a nanochannel or nanopore structure.

At block 310, the method includes forming first and second electrodes that are exposed within the passage and spaced apart from each other to form an electrode gap, wherein the electrode gap is no greater than about 2 nm. The electrodes may be arranged side-by-side or over/under relative to each other. At least one of the electrodes may be movable to alter a size of the gap. The electrodes may be oriented in parallel with the passage, or perpendicular to the passage, or some combination thereof.

At block 315, the method includes measuring an electronic signal using the first and second electrodes as the DNA strand passes through the electrode gap, the electronic signal corresponding to at least one nucleotide of the DNA strand.

Figure 5:
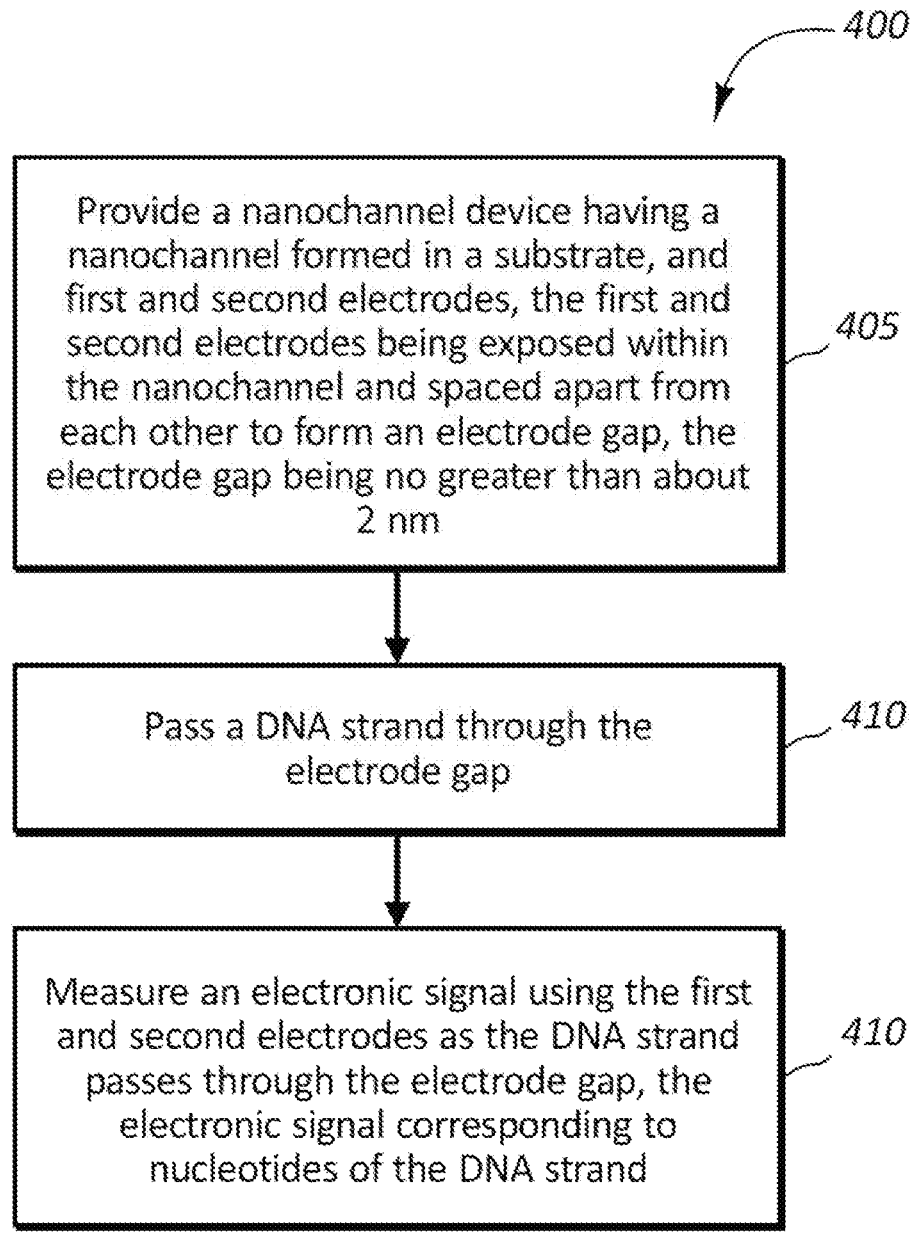
FIG. 5 is a flow diagram illustrating an example method in accordance with the present disclosure.

The DNA sequencing devices 10, 100, 200 disclosed herein may be used to carry out methods of directly sequencing DNA strands. FIG. 5 illustrates steps of an example method 400 that include, at block 405, providing a nanochannel device having a nanochannel formed in a substrate, and first and second electrodes, wherein the first and second electrodes are exposed within the nanochannel and spaced apart from each other to form an electrode gap, and the electrode gap is no greater than about 2 nm. The method 400 also includes, at block 410, passing a DNA strand through the electrode gap. At block 415, the method includes measuring an electronic signal using the first and second electrodes as the DNA strand passes through the electrode gap, wherein the electronic signal corresponds to nucleotides of the DNA strand The example methods 300, 400 may, in other embodiments, include fewer or additional steps that those illustrated in FIGS. 4 and 5. Further, many other methods and method steps may be possible based on the disclosures provided herein.

Figure 6:
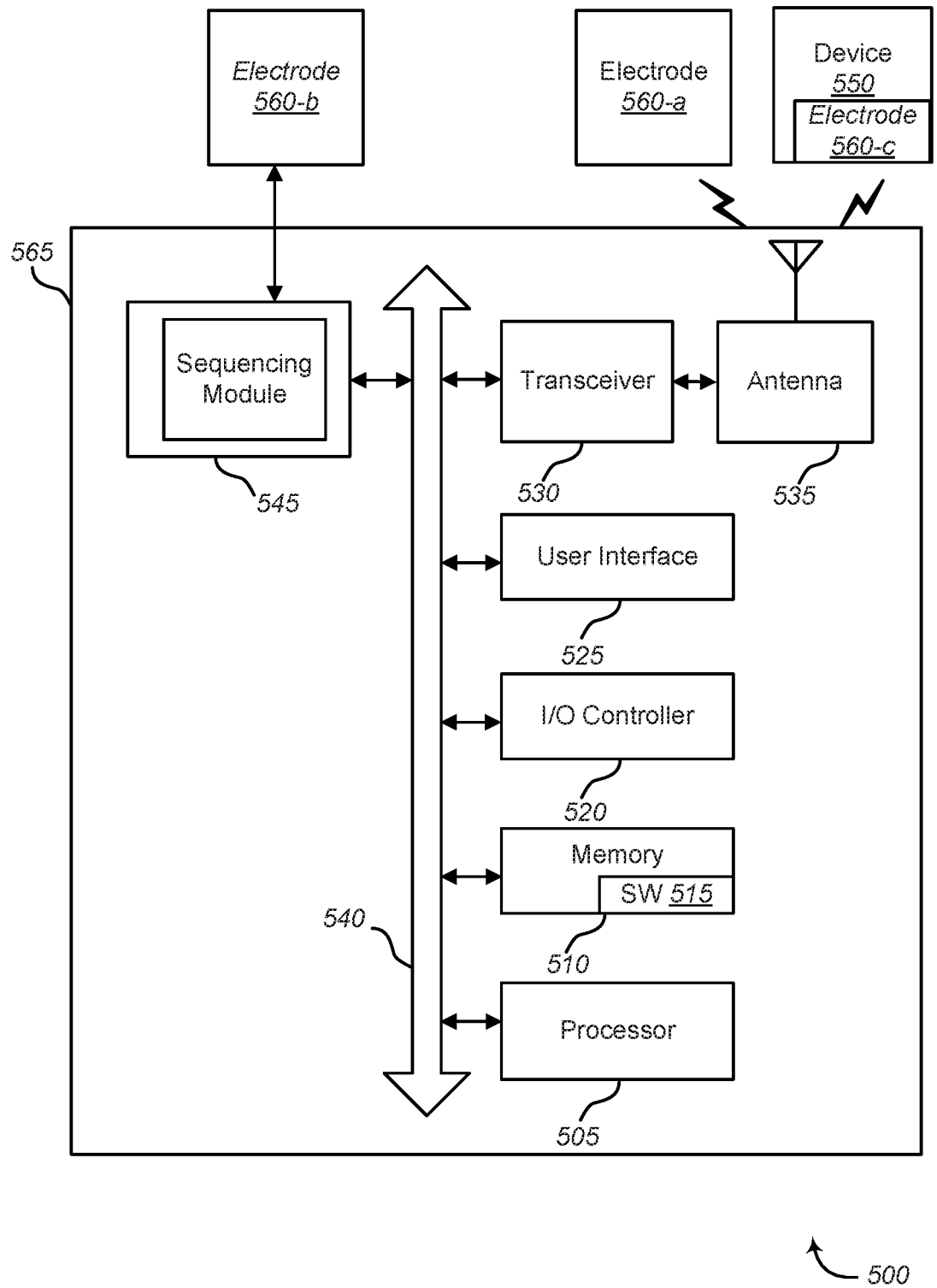
FIG. 6 shows a diagram of a system in accordance with various aspects of this disclosure.

FIG. 6 shows a system 500 for use with the DNA sequencing devices 10, 100, 200 shown in FIGS. 1-3. System 500 may include a control panel 565. Control panel 565 may be equivalent at least in part to a controller, control unit, processor or the like for use with the devices described above with reference to FIGS. 1-3. Control panel 565 may include sequencing module 545. The sequencing module 545 may provide communications with one or more electrodes 560 (also referred to as sensors or devices) directly or via other communication components, such as a transceiver 530 and/or antenna 535. The electrodes 560 may represent one or more of the electrodes 16, 18, 16, 118, 216, 218, or pairs of such electrodes described above. The sequencing module 545 may perform or control various operations associated with, for example, the electrodes, energy source, controller, or other components of the DNA sequencing devices and related systems as described above with reference to FIGS. 1-3.

Control panel 565 may also include a processor module 505, and memory 510 (including software/firmware code (SW) 515), an input/output controller module 520, a user interface module 525, a transceiver module 530, and one or more antennas 535 each of which may communicate, directly or indirectly, with one another (e.g., via one or more buses 540). The transceiver module 530 may communicate bi-directionally, via the one or more antennas 535, wired links, and/or wireless links, with one or more networks or remote devices. For example, the transceiver module 530 may communicate bi-directionally with one or more of device 550 and/or electrodes 560-a, 560-c. The device 550 may be components of the DNA sequencing device 100 and related systems and devices described with reference to FIGS. 1-3, or other devices in communication with such systems and devices. The transceiver 530 may include a modem to modulate the packets and provide the modulated packets to the one or more antennas 535 for transmission, and to demodulate packets received from the one or more antennas 535. In some embodiments (not shown) the transceiver may be communicate bi-directionally with one or more of device 550, remote control device 555, and/or electrodes 560-a, 560-c through a hardwired connection without necessarily using antenna 535. While a control panel or a control device (e.g., 505) may include a single antenna 535, the control panel or the control device may also have multiple antennas 535 capable of concurrently transmitting or receiving multiple wired and/or wireless transmissions. In some embodiments, one element of control panel 565 (e.g., one or more antennas 535, transceiver module 530, etc.) may provide a connection using wireless techniques, including digital cellular telephone connection, Cellular Digital Packet Data (CDPD) connection, digital satellite data connection, and/or another connection.

The signals associated with system 500 may include wireless communication signals such as radio frequency, electromagnetics, local area network (LAN), wide area network (WAN), virtual private network (VPN), wireless network (using 802.11, for example), 545 MHz, Z-WAVE®, cellular network (using 3G and/or LTE, for example), and/or other signals. The one or more antennas 535 and/or transceiver module 530 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 535 may receive signals or information specific and/or exclusive to itself. In other embodiments, each antenna 535 may receive signals or information not specific or exclusive to itself.

In some embodiments, one or more electrodes 560 (e.g., voltage, inductance, resistance, current, force, temperature, etc.) may connect to some element of system 500 via a network using one or more wired and/or wireless connections. In some embodiments, the user interface module 525 may include an audio device, such as an external speaker system, an external display device such as a display screen, and/or an input device (e.g., remote control device interfaced with the user interface module 525 directly and/or through I/O controller module 520).

One or more buses 540 may allow data communication between one or more elements of control panel 565 (e.g., processor module 505, memory 510, I/O controller module 520, user interface module 525, etc.).

The memory 510 may include random access memory (RAM), read only memory (ROM), flash RAM, and/or other types. The memory 510 may store computer-readable, computer-executable software/firmware code 515 including instructions that, when executed, cause the processor module 505 to perform various functions described in this disclosure (e.g., initiating an adjustment of a lighting system, etc.). Alternatively, the software/firmware code 515 may not be directly executable by the processor module 505 but may cause a computer (e.g., when compiled and executed) to perform functions described herein. Alternatively, the computer-readable, computer-executable software/firmware code 515 may not be directly executable by the processor module 505 but may be configured to cause a computer (e.g., when compiled and executed) to perform functions described herein. The processor module 505 may include an intelligent hardware device, e.g., a central processing unit (CPU), a microcontroller, an application-specific integrated circuit (ASIC), etc.

In some embodiments, the memory 510 can contain, among other things, the Basic Input-Output system (BIOS) which may control basic hardware and/or software operation such as the interaction with peripheral components or devices. For example, the sequencing module 545, and other modules and operational components of the control panel 565 used to implement the present systems and methods may be stored within the system memory 510. Applications resident with system 500 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 530, one or more antennas 535, etc.).

Many other devices and/or subsystems may be connected to one or may be included as one or more elements of system 500. In some embodiments, all of the elements shown in FIG. 5 need not be present to practice the present systems and methods. The devices and subsystems can be interconnected in different ways from that shown in FIG. 5. In some embodiments, an aspect of some operation of a system, such as that shown in FIG. 5, may be readily known in the art and are not discussed in detail in this application. Code to implement the present disclosure can be stored in a non-transitory computer-readable medium such as one or more of system memory 510 or other memory. The operating system provided on I/O controller module 520 may be iOS®, ANDROID®, MS-DOS®, MS-WINDOWS®, OS/2®, UNIX®, LINUX®, or another known operating system.

The transceiver module 530 may include a modem configured to modulate the packets and provide the modulated packets to the antennas 535 for transmission and/or to demodulate packets received from the antennas 535. While the control panel or control device (e.g., 505) may include a single antenna 535, the control panel or control device (e.g., 505) may have multiple antennas 535 capable of concurrently transmitting and/or receiving multiple wireless transmissions.

In some embodiments, the DNA sequencing devices described herein may be used to collect electronic signals associated with the nucleotides of a DNA strand passing through the gap between top/bottom electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising:
a passage having a width and a length;
first and second electrodes exposed within the passage and being spaced apart vertically from each other to form an electrode gap, the electrode gap having a height between the first and second electrodes, the height being no greater than about 2 nm, the height of the gap being smaller than the width of the passage, the DNA sequencing device being operable to measure with the first and second electrodes a change in electronic signal in response to nucleotides of a DNA strand passing through the electrode gap.

2. The device of claim 1, wherein at least one of the first and second electrodes is movable to adjust a size of the electrode gap.

3. The device of claim 1, wherein the first electrode is arranged parallel with the length of the passage and the second electrode is arranged perpendicular to the first electrode.

4. The device of claim 1, further comprising a substrate, the passage being formed in the substrate and the first electrode being positioned in the substrate.

5. The device of claim 1, wherein the height of the electrode gap is in the range of about 0.3 nm to about 1 nm.

6. The device of claim 1, wherein the electrodes are positioned vertically relative to each other at locations above and below the passage.

7. The device of claim 1, wherein at least one of the first and second electrodes is embedded in a structure in which the passage is formed.

8. The device of claim 1, wherein at least one of the first and second electrodes is arranged perpendicular to the passage.

9. The device of claim 1, wherein the passage is formed as a nanochannel, the nanochannel having a width in the range of about 5 nm to about 50 nm.

10. A method of forming a device for DNA sequencing, the method comprising:
forming a passage in a substrate, the passage having a width;
forming first and second electrodes, the first and second electrodes being exposed within the passage and vertically spaced apart from each other to form an electrode gap, the electrode gap having a height, the height being no greater than about 2 nm, the height of the gap being smaller than the width of the passage, the electrodes being operable to measure a change in electronic signal as a DNA strand passes through the electrode gap.

11. The method of claim 10, further comprising embedding at least one of the first and second electrodes in the substrate.

12. The method of claim 10, further comprising orienting the first and second electrodes perpendicular to each other.

13. The method of claim 10, wherein the passage is a nanochannel, the method further comprising orienting the first and second electrodes parallel to each other and perpendicular to the nanochannel.

14. The method of claim 10, further comprising orienting the first and second electrodes vertically relative to each other at locations above and below the passage.

15. The method of claim 10, wherein forming the passage includes using at least one of electron-beam lithography (EBL), reactive-ion etching (ME), and spin-on-glass (SOG).

16. The method of claim 10, wherein the passage is a nanochannel, the method further comprising forming the nanochannel with a width in the range of about 5 nm to about 50 nm.

17. A method of sequencing DNA, the method comprising:
providing a DNA sequencing device having a passage formed in a substrate, and first and second electrodes, the passage having a width, the first and second electrodes being exposed within the passage and vertically spaced apart from each other to form an electrode gap, the electrode gap having a height, the height being no greater than about 2 nm, the height of the gap being smaller than the width of the passage;
passing a DNA strand through the electrode gap;
measuring an electronic signal using the first and second electrodes as the DNA strand passes through the electrode gap, the electronic signal corresponding to at least one nucleotide of the DNA strand.

\* \* \* \* \*